(12) United States Patent
Busin

(10) Patent No.: US 12,241,796 B2
(45) Date of Patent: Mar. 4, 2025

(54) THERMOMETER PATCH AND METHODS

(71) Applicant: SEASIGHT TECHNOLOGIES LTD, Rishon Lezion (IL)

(72) Inventor: Shmuel Busin, Rishon Lezion (IL)

(73) Assignee: SEASIGHT TECHNOLOGIES LTD, Rishon le-Zion (IL)

( * ) Notice: Subject to any disclaimer, the term of this patent is extended or adjusted under 35 U.S.C. 154(b) by 714 days.

(21) Appl. No.: 17/433,501

(22) PCT Filed: Feb. 25, 2020

(86) PCT No.: PCT/IL2020/050207
§ 371 (c)(1),
(2) Date: Aug. 24, 2021

(87) PCT Pub. No.: WO2020/174464
PCT Pub. Date: Sep. 3, 2020

(65) Prior Publication Data
US 2022/0155157 A1 May 19, 2022

Related U.S. Application Data

(60) Provisional application No. 62/957,239, filed on Jan. 5, 2020, provisional application No. 62/810,394, filed on Feb. 26, 2019.

(51) Int. Cl.
G01K 13/20 (2021.01)
A61B 5/00 (2006.01)
(Continued)

(52) U.S. Cl.
CPC .............. *G01K 13/20* (2021.01); *A61B 5/01* (2013.01); *A61B 5/688* (2013.01); *G01K 1/14* (2013.01)

(58) Field of Classification Search
None
See application file for complete search history.

(56) References Cited

U.S. PATENT DOCUMENTS 6,547,745 B1  4/2003  Rubinstein
8,325,048 B2 * 12/2012  Ranganathan ........... G01K 3/10
                                                            340/572.1
(Continued)

FOREIGN PATENT DOCUMENTS

CA      2816310 A1 * 12/2005  ........... A61B 5/0002
CN    104382563 A      3/2015
(Continued)

OTHER PUBLICATIONS

English Transaltion of CN 106618513 A, Hangzhou Chuan Hui Medical Treatment Electronic Equipment Co Ltd, 8 pages, printed on Aug. 30, 2024, (Year: 2017).*

*Primary Examiner* — Devin B Henson
*Assistant Examiner* — Jennifer Grace Baires-Tweed
(74) *Attorney, Agent, or Firm* — Allan A. Fanucci

(57) ABSTRACT

The present invention provides devices and methods for measuring the body temperature of a user, and providing audio and/or visual indications upon deviations of said body temperature from predetermined values. The devices of the present invention are further configured to deactivate the various electric components accommodated within said devices following a trigger activation by the user and/or external user, for a predetermined time period.

20 Claims, 5 Drawing Sheets

(51) Int. Cl.
*A61B 5/01* (2006.01)
*G01K 1/14* (2021.01)

(56) References Cited

U.S. PATENT DOCUMENTS

| | | | |
|---|---|---|---|
| 8,380,273 B2 * | 2/2013 | Say | A61B 5/1495 |
| | | | 600/347 |
| 8,663,106 B2 | 3/2014 | Stivoric | |
| 8,922,365 B2 | 12/2014 | Liu | |
| 9,138,144 B2 | 9/2015 | Geva | |
| 9,782,082 B2 | 10/2017 | Gannon | |
| 10,285,617 B2 | 5/2019 | Toth | |
| 2007/0027403 A1 | 2/2007 | Kosted | |
| 2009/0198175 A1 | 8/2009 | Say | |
| 2010/0016681 A1 * | 1/2010 | Charles, Jr. | G16H 40/40 |
| | | | 361/728 |
| 2014/0266694 A1 | 9/2014 | McCluskey | |
| 2015/0223706 A1 | 8/2015 | Raptis | |
| 2015/0335288 A1 | 11/2015 | Toth | |
| 2016/0213354 A1 | 7/2016 | Levin | |
| 2017/0325694 A1 | 11/2017 | Jin | |
| 2018/0055457 A1 | 3/2018 | Balboni | |
| 2018/0184902 A1 | 7/2018 | Meyerson | |
| 2018/0184908 A1 | 7/2018 | Meyerson | |
| 2018/0188114 A1 * | 7/2018 | Ou Yang | G01J 5/041 |
| 2018/0358119 A1 | 12/2018 | Bhushan | |
| 2019/0223749 A1 | 7/2019 | Toth | |

FOREIGN PATENT DOCUMENTS

| | | | | |
|---|---|---|---|---|
| CN | 106562772 A | | 4/2017 | |
| CN | 106618513 A | * | 5/2017 | |
| CN | 108514405 A | | 9/2018 | |
| EP | 3171768 B1 | | 9/2020 | |
| WO | WO-9513016 A1 | * | 5/1995 | A61B 5/208 |
| WO | 2014197822 A2 | | 12/2014 | |
| WO | 2016019250 A1 | | 2/2016 | |
| WO | 2016044881 A1 | | 3/2016 | |
| WO | 2017013582 A1 | | 1/2017 | |
| WO | 2018068068 A2 | | 4/2018 | |
| WO | 2019032245 A1 | | 2/2019 | |
| WO | 2019084156 A1 | | 5/2019 | |

* cited by examiner

THERMOMETER PATCH AND METHODS

FIELD OF THE INVENTION

Provided herein are devices and methods for measuring the body temperature of a user, using a thermometer patch, and providing indications upon a deviation of said body temperature from predetermined values. The devices of the present invention are further configured to deactivate the various electric components accommodated within said devices following a trigger activation by the user and/or external user, for a predetermined time period.

BACKGROUND OF THE INVENTION

Accurately measuring the temperature of an individual, such as an infant, child or a disabled person, is typically performed by utilizing invasive thermometers designed for oral and/or rectal temperature measurements, which can be problematic to conduct while said individual is sleeping or is uncooperative. One solution is utilizing wearable sensors adapted for temperature monitoring of the skin of an individual thereby providing temperature feedback information without the use of intrusive or invasive thermometers.

The use of wearable sensors has been previously suggested. For example, International PCT Publication No. WO 2014/197822 discloses systems, devices, methods, and kits for monitoring one or more physiologic and/or physical signals from a subject, wherein the systems include patches and corresponding modules for wirelessly monitoring physiologic and/or physical signals.

U.S. Pub. No. 2015/0223706 discloses a vital-signs patch for a patient monitoring system, wherein the patch consists of a housing that is configured to be worn on the skin of a patient, the housing contains a radio, one or more sensor interfaces, a processor, and a battery.

International PCT Publication No. WO 2019/084156 discloses monitoring devices useful for detecting, storing, processing or communicating one or more physiologic parameters of the human or animal wearing the monitoring device.

Chinese Publication No. CN 108514405 discloses a body temperature patch comprising a skin-friendly layer contacted with body surface and is arranged such that a first temperature sensing module and integrated circuit modules are adapted to sense the first temperature in real time, and obtain corresponding first temperature.

There remains an unmet need for simple, energy- and cost-efficient methods and devices for measuring the body temperature of a user for continuous extended operation.

SUMMARY OF THE INVENTION

The present invention provides devices and methods for measuring the body temperature of a user, and providing audio and/or visual indications when deviations of said body temperature from predetermined values occur. The devices of the present invention are further configured to deactivate the various electric components accommodated therein upon a trigger activation by the user and/or an external user (such as a caretaker), for a predetermined time period. Advantageously, the disclosed technology enables prolonged continuous operation of said devices and low battery consumption for prolonged duration. Thus, the devices disclosed herein provide a consistent solution for measuring body temperatures of individuals and alerting to their surrounding environment if the measured temperatures are not within a normal range.

Moreover, the devices disclosed herein are simple for manufacturing and use and are of low cost. The simplicity of use is beneficial for the user and/or the external user, as it does not require any adaption or action beyond placing the device on the skin of the user and conducting a first activation thereof.

In some embodiments, the present invention provides an adhesive thermometer patch comprising: an adhesive surface configured to be attached to a skin of a user and an opposing surface; a control unit; a temperature sensor configured to measure temperatures in the range of 30° C. to 45° C., and to transfer temperature signals to said control unit, in response thereto; a power supply unit; an audible indication unit; and a first trigger unit, wherein the adhesive surface and opposing surface form a housing therebetween accommodating at least the control unit and the power supply unit, wherein said control unit is configured to switch from a monitoring state to an alerting state upon the received temperature signals indicating a temperature above a first threshold or below a second threshold, wherein the audible indication unit is deactivated in the monitoring state, wherein the control unit is configured to activate said audible indication unit in the alerting state, and wherein in the alerting state, upon activation of the first trigger unit, the control unit switches from the alerting state to a suspension state for a predetermined time period in the range of 10 minutes to 4 hours, wherein in the suspension state, the control unit is configured to deactivate at least the audible indication unit.

In some embodiments, the control unit is provided in a deactivated state, wherein the first trigger unit is further configured to switch the control unit from the deactivated state to an active state, wherein the active state comprises the alerting state, the suspension state and the monitoring state.

In some embodiments, upon switching from the deactivated state to the active state, the control unit is configured to be in the monitoring state. In some embodiments, the temperature sensor is configured to transfer the temperature signals to the control unit at repeating intervals of every 5 seconds to 5 minutes.

In some embodiments, the adhesive thermometer patch further comprises at least one visual indicator, wherein the control unit is configured to operate the at least one visual indicator to provide a first visual indication, upon receiving each one of the temperature signals, in the monitoring state.

In some embodiments, the control unit is further configured to operate the at least one visual indicator to provide a second visual indication, upon receiving the temperature signals indicating the temperature above the first threshold or below the second threshold, in the alerting state.

In some embodiments, in the suspension state, the control unit is further configured to deactivate the temperature sensor, and the first trigger unit. In further embodiments, in the suspension state, the control unit is further configured to deactivate the temperature sensor, the first trigger unit, and the at least one visual indicator.

In some embodiments, following said predetermined time period, the control unit is configured to switch from the suspension state to the monitoring state.

In some embodiments, the temperature sensor is embedded into a portion of the adhesive surface, so that at least a portion of the temperature sensor is configured to contact the skin of the user, while the adhesive surface is attached to the skin of the user.

In some embodiments, the housing comprises an opening located on the opposing surface, wherein the opposing surface comprises a circumferential external barrier surrounding the opening, extending upwards perpendicularly to the adhesive surface. In some embodiments, the first trigger unit is a push button switch, wherein the circumferential external barrier surrounds the push button switch, thereby preventing accidental activation thereof.

In some embodiments, the control unit comprises at least one processor, a timer, and a memory.

In some embodiments, in the suspension state, said timer is configured to start to measure time for the predetermined time period, and to send a timeout interrupt signal to the processor when the predetermined time period has lapsed, wherein the timeout interrupt signal causes the processor to switch from the suspension state to the monitoring state.

In some embodiments, the processor is configured to switch from a monitoring state to an alerting state upon receiving at least two consecutive temperature signals, each indicating a temperature above the first threshold or below the second threshold.

In some embodiments, the audible indication unit is a buzzer-type alarm.

In some embodiments, the predetermined time period is in the range of 20 to 40 minutes.

In some embodiments, the first threshold is a temperature in the range of 38° C. to 39° C., and the second threshold is a temperature in the range of 35° C. to 36.5° C. In further embodiments, the first threshold is about 38.5° C. and the second threshold is about 35.6° C. The term "about" as used herein when referring to temperatures indicates ±0.2° C., preferably ±0.1° C. of a temperature value. For example, the phrase "the first threshold is about 38.5° C." means that the first threshold may be any temperature value in the range of 38.3° C. to 38.7° C., preferably 38.4° C. to 38.6° C.

In some embodiments, the power supply unit comprises a battery, configured to enable up to about 72 hours of continuous operation for each one of: the temperature sensor, the control unit, the audible indication unit, and the at least one visual indicator. In some embodiments, the battery has a capacity in the range of 200 to 350 mAh.

In some embodiments, the at least one visual indicator comprises a LED lamp. In some embodiments, the LED lamp is configured to display a first color corresponding to the first visual indication, and a second color corresponding to the second visual indication.

In some embodiments, the present invention provides a method for measuring the skin temperature of a user, the method comprising the steps of: (a) providing the adhesive thermometer patch as disclosed herein, and attaching it to the skin of the user; (b) pressing the first trigger unit thereby initializing an activation of the adhesive thermometer patch; (c) performing temperature measurements every 5 seconds to 5 minutes, and transferring temperature signals corresponding thereto to the control unit; (d) determining whether the temperature of the skin of the user is: above a first threshold, below a second threshold, or between the first and the second thresholds; (e) activating the audible indication unit, if the temperature of the skin of the user is above the first threshold or below the second threshold; (f) pressing the first trigger unit, if the audible indication unit is activated, thereby deactivating the audible indication unit and the temperature sensor for a predetermined time period; and (g) reactivating the temperature sensor, following the predetermined time period at step (f).

In some embodiments, step (e) comprises activating the audible indication unit, if the temperature of the skin of the user is above the first threshold or below the second threshold and proceeding to step (f); or returning to step (c), if the temperature of the skin of the user is between the first and the second thresholds.

In some embodiments, if the temperature of the skin of the user is between the first and the second thresholds, the method of the present invention performs steps (a) to (d), and then returns back to step (c). In some embodiments, if the temperature of the skin of the user is above the first threshold or below the second threshold, the method of the present invention performs steps (a) to (g), and then returns back to step (c).

In some embodiments, the adhesive thermometer patch further comprises at least one LED lamp, wherein step (c) further comprises displaying a first visual indication by the at least one LED lamp during temperature measurements, and wherein step (e) comprises displaying a second visual indication by the at least one LED lamp during the audible indication unit activation.

In some embodiments, step (g) further comprises returning to step (c).

In some embodiments, the present invention provides a method for measuring the skin temperature of a user, the method comprising the steps of: (a) providing an adhesive thermometer patch and attaching it to the skin of the user, wherein the adhesive thermometer patch comprises: a control unit; a temperature sensor; an audible indication unit; and a first trigger unit; (b) pressing the first trigger unit thereby initializing an activation of the adhesive thermometer patch, wherein the activation comprises activating the control unit and the temperature sensor; (c) performing temperature measurements of the skin of the user every 5 seconds to 5 minutes using the temperature sensor, and transferring temperature signals corresponding thereto to the control unit; (d) determining whether the temperature of the skin of the user is: above a first threshold, below a second threshold, or between the first and the second thresholds; (e) activating the audible indication unit, if the temperature of the skin of the user is above the first threshold or below the second threshold; (f) pressing the first trigger unit if the audible indication unit is activated, thereby deactivating the audible indication unit for a predetermined time period; and (g) reactivating the temperature sensor, following the ending of the predetermined time period at step (f).

In some embodiments, the adhesive thermometer patch further comprises a power supply unit, an adhesive surface and an opposing surface, wherein the adhesive surface and the opposing surface form a housing therebetween accommodating at least one of the control unit and the power supply unit.

In some embodiments, the adhesive thermometer patch further comprises at least one visual indicator, and step (c) further comprises providing a first visual indication by the at least one visual indicator. In some embodiments, the at least one visual indicator comprises at least one LED lamp, and the first visual indication comprises a flashing green light.

In some embodiments, step (c) comprises performing temperature measurement of the skin of the user every about 30 seconds. In some embodiments, during step (c) the audible indication unit is deactivated.

In some embodiments, step (d) comprises determining whether the temperature of the skin of the user is: above a first threshold, below a second threshold, or between the first and the second thresholds, by the control unit based on temperature signals transferred thereto in step (c). In some embodiments, the first threshold is a temperature in the range of 38° C. to 39° C., and the second threshold is a temperature in the range of 35° C. to 36.5° C.

In some embodiments, step (e) comprises activating the audible indication unit, if the temperature of the skin of the user is above the first threshold or below the second threshold and proceeding to step (f); or returning to step (c), if the temperature of the skin of the user is between the first and the second thresholds. In some embodiments, in step (e) the activation of the audible indication unit is performed by the control unit. In some embodiments, step (e) further comprises providing a second visual indication by the at least one visual indicator. In some embodiments, the at least one visual indicator is at least one LED lamp, and the second visual indication comprises a flashing red light.

In some embodiments, if the temperature of the skin of the user is between the first and the second thresholds, the method of the present invention performs steps (a) to (d), and then returns back to step (c). In some embodiments, if the temperature of the skin of the user is above the first threshold or below the second threshold, the method of the present invention performs steps (a) to (g), and then returns back to step (c).

In some embodiments, the pressing of the first trigger unit in step (f) causes the control unit to deactivate the audible indication unit for the predetermined time period. In some embodiments, pressing the first trigger unit in step (f) causes the control unit to further deactivate at least one of the temperature sensor, and the first trigger unit. In some embodiments, in step (f) pressing the first trigger unit causes the control unit to deactivate the at least one visual indicator. In some embodiments, the predetermined time period in step (f) is in the range of 20 to 40 minutes.

In some embodiments, the reactivation of the temperature sensor in step (g) is performed by the control unit. In some embodiments, step (g) further comprises reactivating the at least one visual indicator by the control unit. In some embodiments, step (g) further comprises returning to step (c).

Further advantages of the devices and methods disclosed herein may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION

Figure 1A:
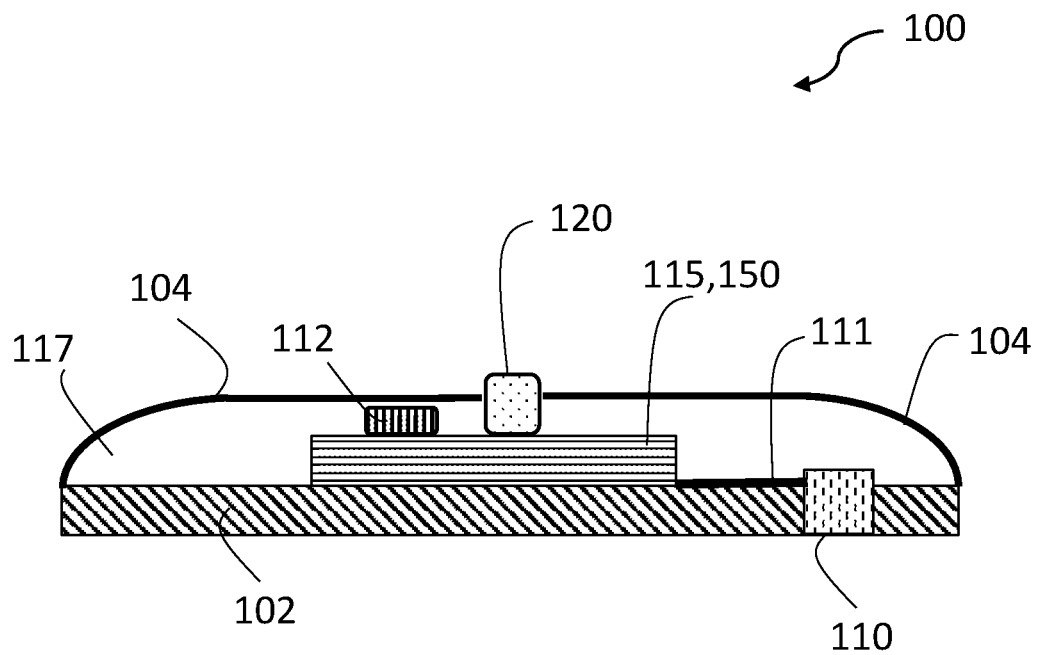
FIGS. 1A-1D illustrate cross-sectional views of adhesive thermometer patch 100, through different embodiments of the present invention.

The present invention provides patches and methods for measuring the body temperature of a user, and providing at least one indication regarding a deviation of said body temperature from predetermined threshold values. The devices of the present invention are further configured to deactivate the various electric components accommodated within said devices upon a trigger activation by the user or an external user, for a predetermined time period, after which operation is resumed.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts throughout.

Figure 2A:
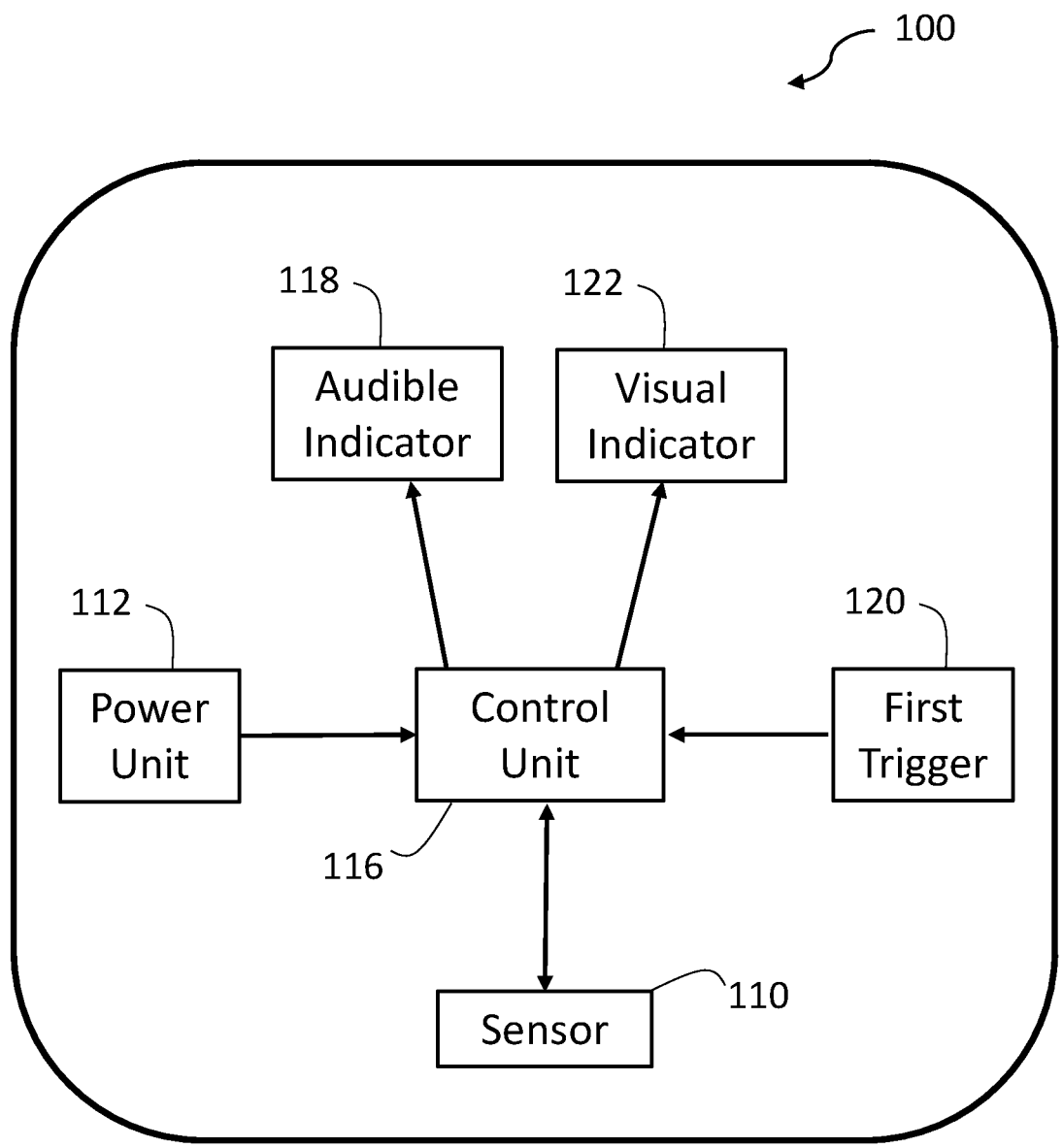
FIG. 2A constitutes a functional block diagram depicting patch 100 through different embodiments of the present invention.
Figure 2B:
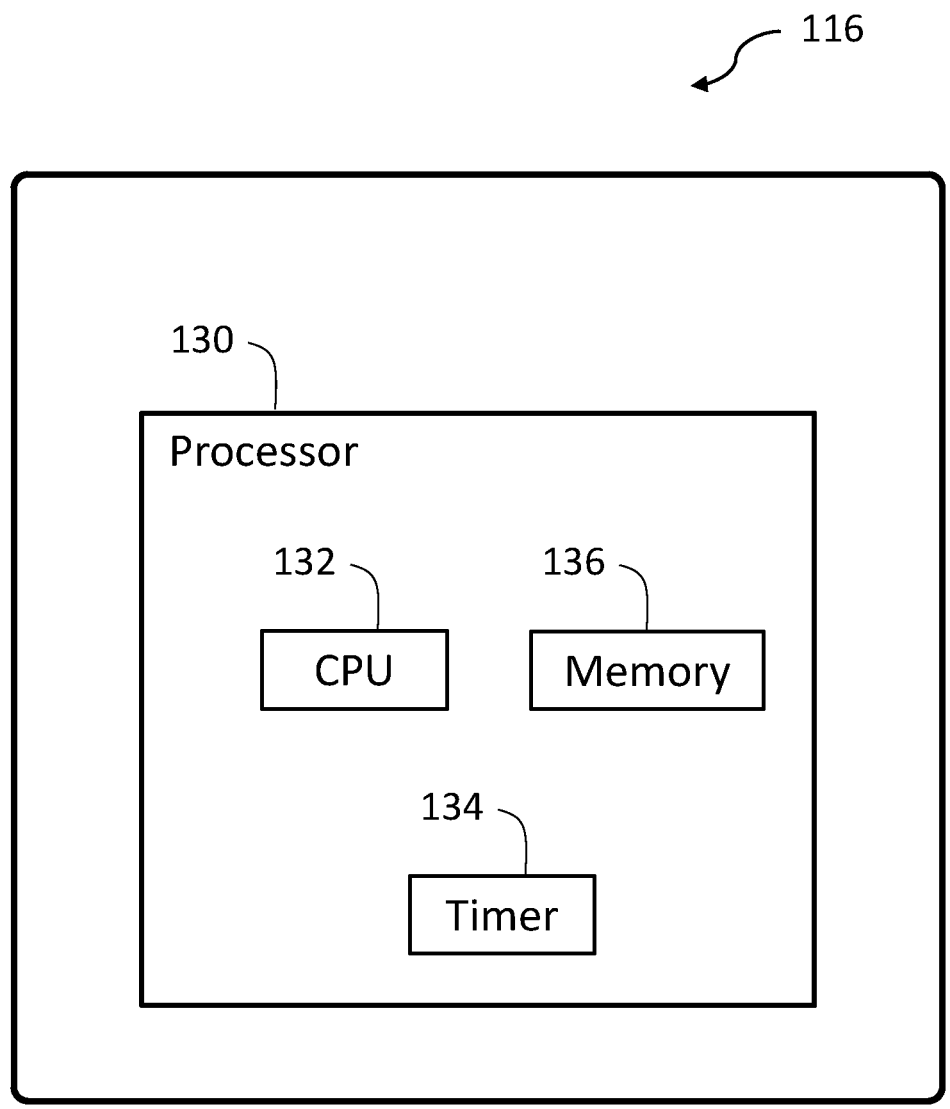
FIG. 2B constitutes a functional block diagram depicting control unit 116 of FIG. 2A, in some embodiments of the present invention.
Figure 3:
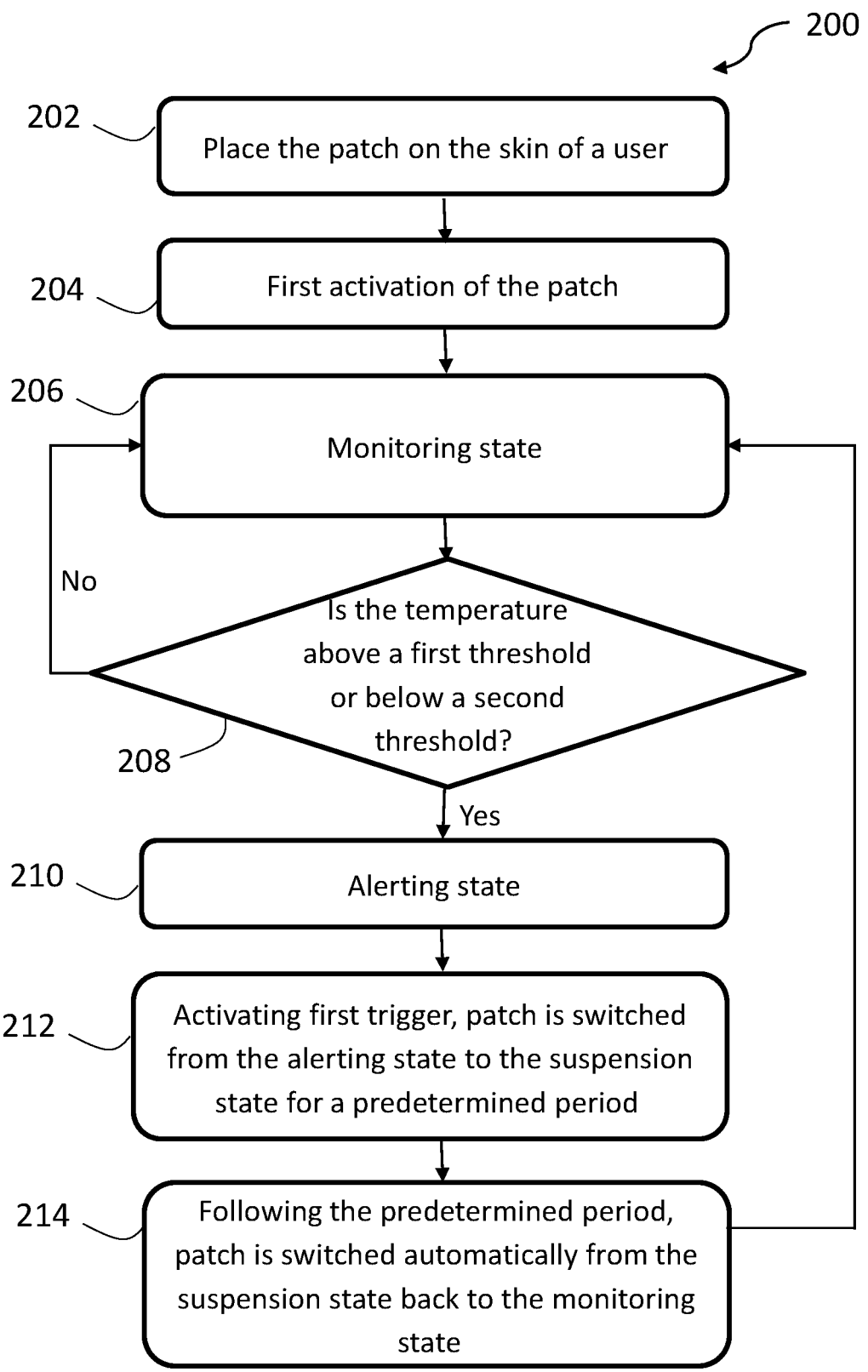
FIG. 3 is a flowchart of a method for measuring the body temperature of a user, in some embodiments of the present invention.

According to some embodiments, there is provided an adhesive thermometer patch 100. Reference is now made to FIGS. 1A-1D, 2A-2B and 3. FIGS. 1A-1D illustrate cross-sectional views of adhesive thermometer patch 100, through different embodiments of the present invention. FIG. 2A constitutes a functional block diagram depicting adhesive thermometer patch 100 in some embodiments of the present invention. FIG. 2B constitutes a functional block diagram depicting control unit 116 of FIG. 2A, in some embodiments of the present invention. FIG. 3 is a flowchart of a method for measuring the body temperature of a user, in some embodiments of the present invention.

Adhesive thermometer patch 100 comprises an adhesive surface 102 and an opposing surface 104, wherein adhesive surface 102 and opposing surface 104 together form a housing 117 therebetween accommodating inner components of adhesive thermometer patch 100, including a circuit assembly 115, a power supply unit 112, at least a portion of a first trigger unit 120, a temperature sensor 110 and a connecting circuit 111, as illustrated in FIG. 1A. In some embodiments, housing 117 is configured to provide mechanical protection to the inner components of adhesive thermometer patch 100 accommodated within. In some embodiments, power supply unit 112 is in electrical communication with circuit assembly 115 and temperature sensor 110. In some embodiments, first trigger unit 120 is in operational communication with at least circuit assembly 115. In some embodiments, circuit assembly 115 is in operational communication with temperature sensor 110.

Temperature sensor 110 is attached to adhesive surface 102. In some embodiments, temperature sensor 110 is embedded into a portion of adhesive surface 102. In some embodiments, temperature sensor 110 is extending through a portion of adhesive surface 102, so that at least a portion of temperature sensor 110 is exposed through adhesive thermometer patch 100. In some embodiments, at least a portion of temperature sensor 110 is configured to contact the skin of a user, while adhesive surface 102 is attached to the skin of the user. Circuit assembly 115 is disposed between adhesive surface 102 and opposing surface 104. In some embodiments, circuit assembly 115 comprises various electronic components and power supply unit 112 (shown in FIG. 1A) mounted to a printed circuit board (PCB) 150. Power supply unit 112 can be located either between said PCB 150 and opposing surface 104, or embedded within a socket of PCB 150. In some embodiments, circuit assembly 115 is in operational communication with temperature sensor 110 via the connecting circuit 111. In some embodiments, connecting circuit 111 operably connects the temperature sensor 110 to the circuit assembly 115. The connecting circuit 111 can be one or more wire traces on PCB 150.

In some embodiments, housing 117 is adapted to be thin, flexible, and soft, in order to provide wear comfort to the user and to successfully be attached to the curvilinear shape of the skin of the user. In some embodiments, each one of circuit assembly 115, PCB 150, and connecting circuit 111 is flexible. In some embodiments, adhesive surface 102 and opposing surface 104 comprises an elastic material, thereby enabling adhesive thermometer patch 100 to maintain its operation when stretched or bent to more than about 10%, more than about 25%, or more than about 50% of its original length.

In some embodiments, adhesive surface 102 and opposing surface 104 are water resistant. In some embodiments, housing 117 is water resistant.

In some embodiments, circuit assembly 115 is substantially rigid. In some embodiments, PCB 150 is substantially rigid.

Figure 1B:
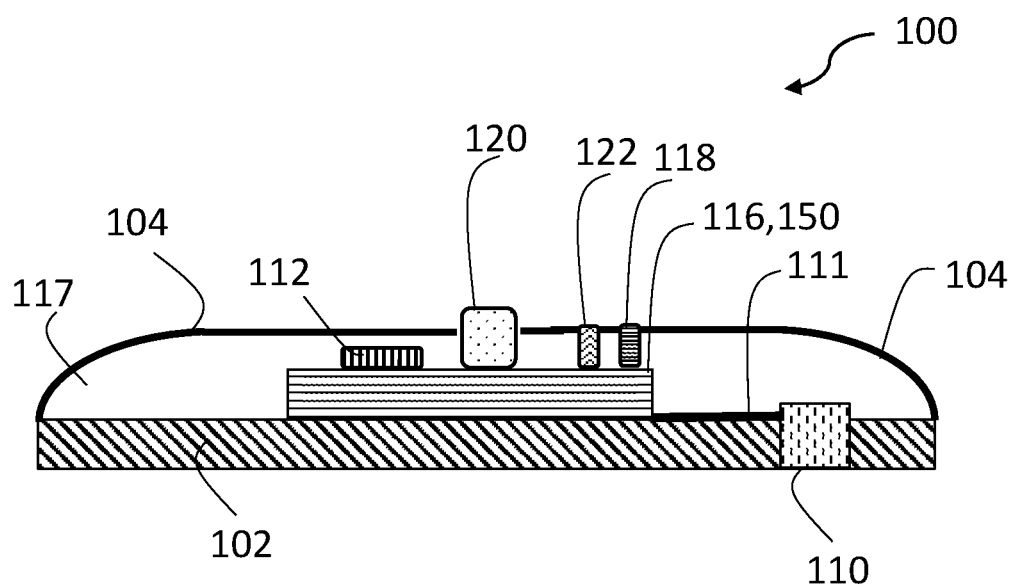

FIG. 1B illustrates yet another embodiment of the adhesive thermometer patch 100 which differs from the embodiment of FIG. 1A in that circuit assembly 115 comprises a control unit 116, an audible indication unit 118, and at least one visual indicator 122. In some embodiments, control unit 116 is in operational communication with audible indication unit 118, temperature sensor 110, and at least one visual indicator 122. In some embodiments, power supply unit 112 is in electrical communication with a control unit 116, audible indication unit 118, temperature sensor 110 and at least one visual indicator 122. In some embodiments, control unit 116 is in operational communication with temperature sensor 110 via the connecting circuit 111.

In some embodiments, opposing surface 104 further comprises an opening (not shown) adapted to enable at least a portion of the at least one visual indicator 122 to be visibly noticed from the outside of adhesive thermometer patch 100. In some embodiments, at least one visual indicator 122 is configured to provide a visual indication, wherein the visual indication is visible through an opening in opposing surface 104. In some embodiments, opposing surface 104 further comprises at least one opening (not shown) adapted to enable at least a portion of audible indication unit 118 to release sound outside of adhesive thermometer patch 100. In some embodiments, audible indication unit 118 is configured to provide a sound indication through an opening in opposing surface 104.

In some embodiments, first trigger unit 120 is a push button switch. In some embodiments, opposing surface 104 further comprises an opening adapted to enable at least a portion of the first trigger unit 120 to be visibly noticed from the outside of adhesive thermometer patch 100, wherein said at least a portion of the first trigger unit 120 is configured to be activated by the user.

The term "push button switch" as used herein refers to a button mechanism, wherein a first press of the push button actuates the patch from 'off' to 'on' and activates the various components of adhesive thermometer patch 100.

In some embodiments, adhesive thermometer patch 100 is in the form of a sticker, a band-aid or a sticker-like configuration. Adhesive thermometer patch 100 can be designed with a variety of external shapes and dimensions, configured to adapt for reversible attachment to the skin of the user. The adhesive thermometer patch 100 can be applied to various sections on the body of the user such as, but not limited to, the upper chest, arm pit, clavicle, forehead, neck, abdomen, feet, and other functional areas thereof. In some embodiments, adhesive thermometer patch 100 is applied to various sections on the body of the user that typically maintains a fairly stable temperature such as, but not limited to, the arm pit or the forehead.

In some embodiments, adhesive surface 102 is configured to be attached to a skin of a user using a standard biocompatible adhesive material. In some embodiments, adhesive surface 102 is configured to affix adhesive thermometer patch 100 to the skin of the user. In some embodiments, adhesive surface 102 is configured to be reversibly attached to the skin of the user. In some embodiments, adhesive surface 102 is configured to be removed and re-applied at least twice to the skin of the user. In some embodiments, adhesive surface 102 is configured to be removed and re-applied at least three times, at least four times, at least five times, or at least ten times to the skin of the user. In some embodiments, adhesive surface 102 is configured to be removed and re-applied a plurality times to the skin of the user, without affecting its adhesive capabilities or characteristics as disclosed herein.

In some embodiments, adhesive surface 102 is water resistant, such that adhesive thermometer patch 100 remains attached to the skin of the user, when in contact with water.

It is to be understood that the attachment of adhesive thermometer patch 100 to the body of the user is primarily induced by adhesive attachment, and not by any wearable configuration such as a jewelry or a clothing article. Advantageously, the lack of wearable configurations can contribute to the cost effective and/or simple manufacture and use of the adhesive thermometer patch 100.

In some embodiments, housing 117 is accommodating temperature sensor 110, power supply unit 112, control unit 116, audible indication unit 118, first trigger unit 120 and at least one visual indicator 122, as illustrated at FIG. 1B. In some embodiments, control unit 116, audible indication unit 118, at least one visual indicator 122, power supply unit 112, and first trigger unit 120 are accommodated within housing 117, and are in a close proximity to temperature sensor 110.

The term "close proximity" as used herein, refers to a distance of less than about 1 cm, preferably less than about 5 mm, or more preferably less than about 1 mm.

Figure 1C:
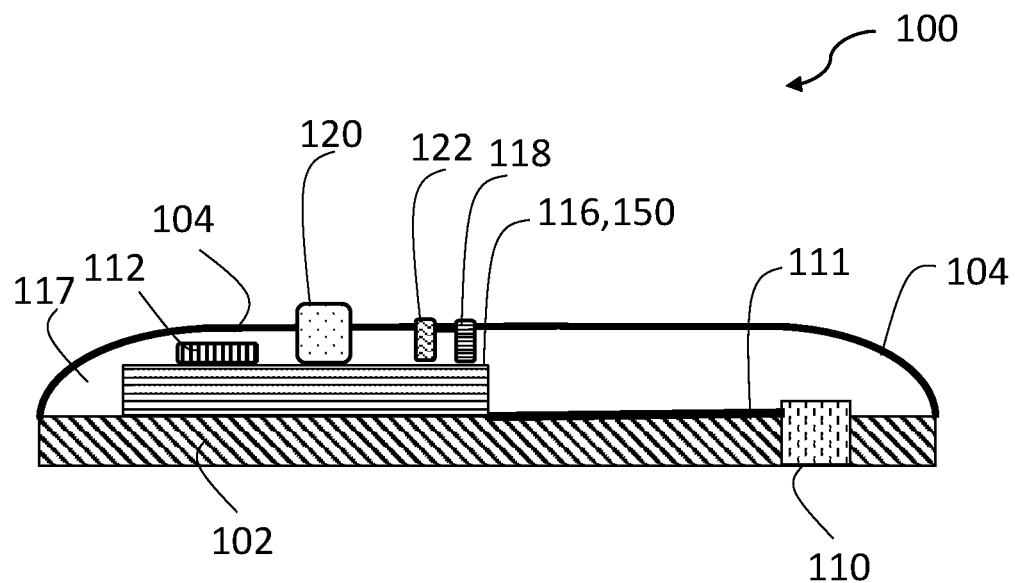

FIG. 1C illustrates yet another embodiment of the adhesive thermometer patch 100 which differs from the embodiments of FIG. 1B in that control unit 116, audible indication unit 118, at least one visual indicator 122, power supply unit 112, and first trigger unit 120 are further distanced from temperature sensor 110.

The term "further distanced" as used herein, refers to a distance of more than about 1 cm, preferably more than about 1.5 cm, or more preferably more than about 2 cm.

Figure 1D:
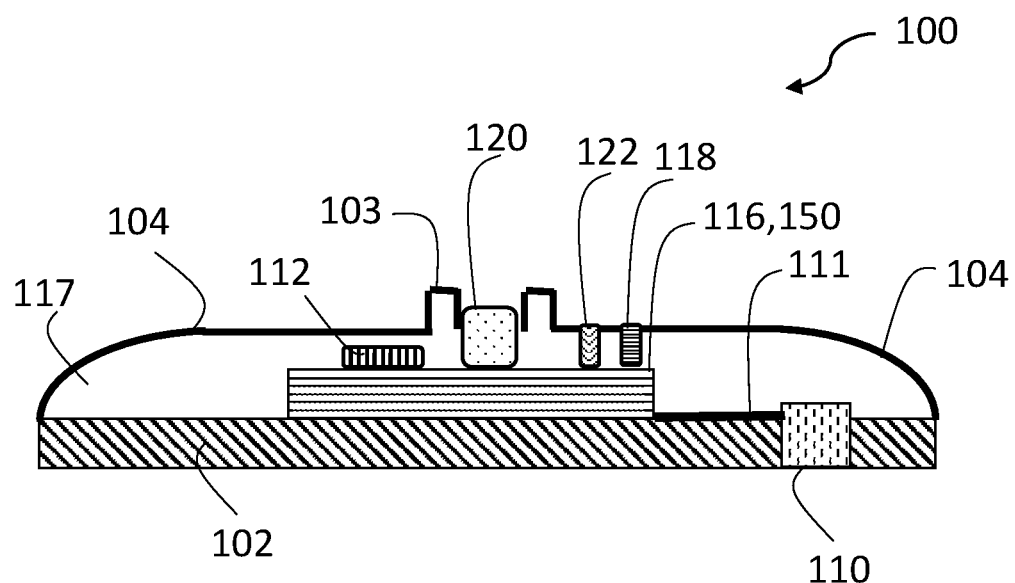

FIG. 1D illustrates yet another embodiment of the adhesive thermometer patch 100 which differs from the embodiments of FIG. 1B in that housing 117 comprises an opening located on the opposing surface 104, wherein the opposing surface 104 comprises a circumferential external barrier 103 surrounding the opening, extending perpendicularly to adhesive surface 102. In some embodiments, first trigger unit 120 is disposed between the circumferential external barrier 103 and a portion of control unit 116, and is configured to be activated by the user and/or external user. In some embodiments, circumferential external barrier 103 surrounds first trigger unit 120.

In some embodiments, first trigger unit 120 is a push button switch. In some embodiments, circumferential external barrier 103 surrounds the push button switch, thereby preventing accidental activation thereof. Advantageously, circumferential external barrier 103 provides rigidity to the first trigger unit 120, thereby preventing accidental activation of the first trigger unit 120. Specifically, as adhesive thermometer patch 100 may be used, e.g. for temperature measurements of babies and toddlers, it is beneficial that a barrier will prevent accidental events, which may affect the indication process.

Reference is now made to FIG. 2A. In some embodiments, adhesive thermometer patch 100 illustrated at FIG. 2A is substantially identical to adhesive thermometer patch 100 illustrated at each one of FIGS. 1A-1D.

In some embodiments, temperature sensor 110 is configured to measure the temperature of the skin of said user, and to transfer temperature signals to control unit 116, in response thereto. In some embodiments, control unit 116 is configured to switch from a monitoring state to an alerting state upon receiving temperature signals indicating a temperature above a first threshold or below a second threshold. In some embodiments, control unit 116 is configured to switch from a monitoring state to an alerting state upon receiving at least two consecutive temperature signals indicating a temperature above a first threshold value or below a second threshold value. In some embodiments, audible indication unit 118 is deactivated in the monitoring state. In some embodiments, control unit 116 is configured to activate audible indication unit 118 in the alerting state. In some embodiments, in the alerting state, upon activation of first trigger unit 120, control unit 116 switches from the alerting state to a suspension state for a predetermined time period, in the range of 10 minutes to 4 hours, including each value within the specified range.

In some embodiments, in the suspension state, the control unit 116 is configured to deactivate at least the audible indication unit 118. In some embodiments, in the suspension state, the control unit 116 is further configured to deactivate temperature sensor 110, first trigger unit 120, and at least one visual indicator 122. In some embodiments, following said predetermined time period, the control unit 116 is configured to switch from the suspension state to the monitoring state, and to resume the operation of at least the temperature sensor 110. In some embodiments, following said predetermined time period, the control unit 116 is configured to switch from the suspension state to the monitoring state, and further resume the operation of first trigger unit 120 and the at least one visual indicator 122.

In some embodiments, control unit 116 is provided to the user in a deactivated state, wherein the first trigger unit 120 is further configured to switch the control unit from the deactivated state to an active state. In some embodiments, the active state comprises the alerting state, the suspension state, and the monitoring state.

The inventor of the present invention has developed an advantageous patch for measuring the temperature of a user (for example, a sick child or an infant) without utilizing the use of invasive thermometers. Said patch can indicate once the body of the user reaches a critical temperature, i.e. switch from a monitoring state to an alerting state, wherein said critical temperature can suggest a dangerous medical condition, such as for example, hyperthermia or hypothermia. Said indication can alarm external users (i.e. parents or a caretaker) of the condition of the user wearing the patch.

The term "critical temperature", as used herein, refers to a temperature above the first threshold or below the second threshold.

Additionally, the inventor of the present invention has added a beneficial component featuring a first trigger unit 120, which is configured to be activated by the user/external users and to cause control unit 116 to switch from the alerting state to a suspension state for a predetermined time period.

After alarming the user or external users about the condition of the user wearing the patch, said user or external users can activate first trigger unit 120, thereby causing control unit 116 to switch from the alerting state to the suspension state, in order to deactivate the audible indication unit 118, and to provide treatment to said user, for example by administering a fever-reducing medication. Following the predetermined time period, control unit 116 switches from the suspension state back to the monitoring state, and the patch resumes its operation and continues to measure the temperature of the user. The patch can then indicate whether the administered medication or treatment have succeeded in bringing the temperature back to a normal body temperature.

The term "normal body temperature" as used herein, refers to a temperature of the skin of a user which is between the first threshold and the second threshold.

In some embodiments, the first threshold is a temperature selected from the range of about 37.6 to about 40° C. In further embodiments, the first threshold is a temperature selected from the range of about 38 to about 39° C. In some embodiments, the first threshold is about 38.5° C. In some embodiments, the second threshold is a temperature selected from the range of about 35 to about 36.5° C. In some embodiments, the second threshold is about 35.6° C.

Without wishing to being bound to any mechanism of action, it is contemplated that the inventor of the present invention has developed a cost effective, simple, and accurate adhesive thermometer patch 100 which is configured to provide visual and/or audio indications once the body of a user reaches hyperthermia or high fever (i.e. a temperature above 38.5° C.) or hypothermia (i.e. a temperature below 35.6° C.).

In some embodiments, the audible indication unit 118 is configured to provide an audio indication once the temperature of the body of the user is above about 38.5° C. or is below about 35.6° C.

It should also be understood that the adhesive thermometer patch 100 does not include any wired or wireless communication or connectivity unit, such as internet connectivity or Bluetooth transmitter. Advantageously, the lack of wired, wireless communication, or connectivity units, can contribute to the cost effective and/or simple manufacture of the adhesive thermometer patch 100. In addition, as disclosed herein, a beneficial feature of the thermometer patch disclosed herein is that it is durable for at least 72 hours. This important feature is, in some embodiments, attributed to the low power consumption of adhesive thermometer patch 100, which is devoid of power consuming electronics, such as communication devices. In some embodiments, adhesive thermometer patch 100 is devoid of any communication devices with external electronic devices.

In some embodiments, adhesive thermometer patch 100 is also devoid of any visual display indicator, e.g. a display screen. In alternative embodiments, the adhesive thermometer patch 100 comprises a visual display indicator configured to display the measured body temperature of the user, wherein said visual display indicator optionally comprises a display screen.

Reference is now made to FIG. 2B. In some embodiments, control unit 116 comprises at least one processor 130 configured to send and receive data (such as, but not limited to, digitized signal, control data, and temperature signals) to and from the various electronic components of the adhesive thermometer patch 100. At least one processor 130 can be selected from, but not limited to, a microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information. In some embodiments, processor 130 comprises a central processing unit (CPU) 132, a timer 134, and a memory 136. In further embodiments, CPU 132, timer 134 and memory 136 are embedded within the at least one processor 130, as illustrated at FIG. 2B.

The term "processor", as used herein, refers to a single chip device which includes a plurality of modules which may be collected onto a single chip in order to perform various computer-related functions. In particular, processor 130 can include a CPU module, a memory module and a timer module, together with optional additional integral circuit modules. In some embodiments, processor 130 comprises a set of software algorithms configured to carry out measurements, indications, and recordings of functional events.

The term "memory", as used herein, refers to any suitable data storage component for storing temperature signals data and/or software algorithms, including volatile memory types such as, but not limited to, random access memory, DRAM, and SDRAM, or non-volatile memory types such as, but not limited to, flash memory, read-only memory (ROM), and ferroelectric RAM. In some embodiments, processor 130 accesses the temperature signals data stored at memory 136, and compares current temperature signals readings with previously measured temperature signals.

The term "timer", as used herein, refers to a software embedded feature, which upon activation is adapted to measure time according to a pre-determined schedule.

The term "software algorithms", as used herein, refers to a sequence of instructions configured for execution by processor 130. Software algorithms can include a subroutine, a function, a procedure, an object method, an object implementation, an executable application, an applet, a servlet, a source code, an object code, a shared library/ dynamic load library and/or other sequence of instructions designed for execution by a processing system.

As used herein, the term "deactivated state" refers to the initial state of adhesive thermometer patch 100 prior to first activation by the user or an external user, i.e. prior to initializing the first usage of power supply unit 112 and/or control unit 116. In some embodiments, during the deactivated state, all of the electric components accommodated within adhesive thermometer patch 100 are deactivated. In some embodiments, during the deactivated state the temperature sensor 110, control unit 116, audible indication unit 118, and at least one visual indicator 122 are deactivated.

In some embodiments, upon switching from the deactivated state to the active state, control unit 116 is configured to be in the monitoring state. In some embodiments, upon switching from the deactivated state to the active state, processor 130 is configured to be in the monitoring state.

As used herein, the term "monitoring state" refers to a state in which temperature sensor 110 is configured to measure the temperature of the skin of said user, and to transfer temperature signals to processor 130, in response thereto. In some embodiments, in the monitoring state, the temperature sensor 110, control unit 116, and at least one visual indicator 122 are active. In some embodiments, in the monitoring state, the audible indication unit 118 is deactivated. In some embodiments, the activation of first trigger unit 120 during the monitoring state wherein the temperature of the user is between the first threshold and the second threshold will not generate any effect on adhesive thermometer patch 100.

In some embodiments, temperature sensor 110 comprises a thermometer, configured to measure human body temperatures. In some embodiments, the temperature sensor 110 is configured to measure temperatures in the range of 30° C. to 45° C. In some embodiments, the temperature sensor 110 is configured to measure temperatures in the range of 34° C. to 42° C. In some embodiments, the temperature sensor 110 is selected from the group consisting of: a thermocouple, a resistance temperature detector (RTD or PT100), a thermistor, a solid-state sensor, and any other temperature sensor known in the art.

It is to be understood that each temperature measurement of temperature sensor 110 has a temperature measurement duration. In some embodiments, the temperature measurement duration of temperature sensor 110 is less than about 1 second. In further embodiments, the temperature measurement duration of temperature sensor 110 is less than about 0.5 seconds. In still further embodiments, the temperature measurement duration of temperature sensor 110 is less than about 0.3 seconds.

In some embodiments, adhesive thermometer patch 100 comprises a plurality of temperature sensors 110, wherein each temperature sensor 110 is attached to adhesive surface 102 at a different location.

In some embodiments, temperature sensor 110 is configured to measure the temperature of the skin or the body of the user, and to send out a periodic 'interrupt' signal comprising a temperature signal at repeating intervals to processor 130, in order to prevent continuous temperature measurement and to extend the utilization of power supply unit 112. In further embodiments, the repeating intervals occur every about 5 seconds to about 5 minutes. In some embodiments, the temperature sensor 110 is configured to transfer the temperature signals to processor 130 at repeating intervals of every about 5 seconds to about 5 minutes. In still further embodiments, the repeating intervals occur every about 15 to about 40 seconds. In yet still further embodiments, temperature sensor 110 is configured to send out an 'interrupt' signal comprising a temperature signal every about 30 seconds to processor 130.

In some embodiments, temperature sensor 110 is configured to measure the temperature of the skin or the body of the user within less than about 0.5 second and to send out periodic 'interrupt' signals comprising the temperature signal every about 30 seconds to processor 130.

Advantageously, a measurement of the temperature within gaps of 5 seconds to 5 minutes, preferably 15 to 40 seconds, or more preferably with gaps of about 30 seconds, was found sufficient for temperature monitoring during the monitoring state, while saving energy, through a low power consumption regime.

The "continuous" measurement of the skin temperature of the user is frequently periodic, in that measurements are taken at repeating intervals. For the purpose of temperature measurement, a sequence of repeated measurements can be considered to be "continuous" when the temperature is not likely to change in an amount that is of clinical significance within the interval between consecutive measurements. As used herein, the term "continuous measurement of the skin temperature" refers to temperature measurements taken at repeating intervals occurring every 15 to 40 seconds, or more preferably every about every 30 seconds.

As used herein, the term "interrupt signal" refers to an input signal to processor 130 indicating an event that needs immediate attention. An interrupt signal alerts processor 130 and serves as a request for interrupting the currently executing code, so that the event can be processed, and further functions can be executed.

In some embodiments, processor 130 is configured to operate the at least one visual indicator 122 to provide a first visual indication, upon receiving each one of the temperature signals, in the monitoring state. In further embodiments, the at least one visual indicator 122 comprises a LED lamp. In still further embodiments, the LED lamp is configured to display a first color corresponding to the first visual indication. In yet still further embodiments, the LED lamp is configured to provide a first visual indication comprising a flashing green light during temperature measurement, in the monitoring state.

As used herein, the term "alerting state" refers to a state in which processor 130 is configured to activate audible indication unit 118, upon receiving temperature signals indicating a temperature above a first threshold or below a second threshold. In some embodiments, in the alerting state, the audible indication unit 118 and at least one visual indicator 122 are active.

In some embodiments, processor 130 is configured to switch from the monitoring state to the alerting state upon receiving at least two consecutive temperature signals, each indicating a temperature above the first threshold or below the second threshold. In some embodiments, in order to identify at least two consecutive temperature signals, each indicating a temperature above the first threshold or below the second threshold, processor 130 is configured to access the temperature signals stored at memory 136 and compare the current temperature signal with at least one previous temperature signal.

In some embodiments, processor 130 is further configured to operate the at least one visual indicator 122 to provide a second visual indication, upon receiving the temperature signals indicating the temperature above the first threshold or below the second threshold, in the alerting state. In further embodiments, the LED lamp is configured to display a second color corresponding to the second visual indication. In some embodiments, the LED lamp is configured to provide a second visual indication comprising a flashing red light, during the alerting state.

In some embodiments, the second visual indication and the first visual indication are identical, and comprise displaying the same color during the monitoring state and the alerting state.

As used herein, the term "suspension state" refers to a state in which processor 130 deactivates: audible indication unit 118, temperature sensor 110, first trigger unit 120, and at least one visual indicator 122.

In some embodiments, upon activation of the first trigger unit 120 by the user or external users during the alerting state, processor 130 switches from the alerting state to the suspension state and timer 134 starts to measure time until the predetermined time period has lapsed. In further embodiments, timer 134 is configured to send a timeout 'interrupt' signal to processor 130 after the predetermined time period is over, thereby causing processor 130 to switch from the suspension state back to the monitoring state.

As used herein, the term "timeout 'interrupt' signal" refers to an input signal issued by timer 134 to processor 130, indicating that the predetermined time period has lapsed.

In some embodiments, audible indication unit 118 comprises a buzzer-type alarm. In some embodiments, the activation of audible indication unit 118 during the alerting state comprises activating said buzzer-type alarm. In some embodiments, processor 130 is configured to maintain/continue the activation of audible indication unit 118 during the alerting state, until the activation of first trigger unit 120 by the user or external users.

In some embodiments, an additional activation of first trigger unit 120 by the user or external users after commencing but prior to the ending of the predetermined time period will not resume the operation of the various components of adhesive thermometer patch 100, i.e. will not cause processor 130 to switch from the suspension state back to the monitoring state.

It should be noted, that the first trigger unit 120 is configured to be activated by the user/external users and to cause processor 130 to switch from the alerting state to the suspension state, solely following the activation of audible indication unit 118 in the alerting state, indicating a temperature above a first threshold or below a second threshold. If the temperature signals indicate a normal body temperature, which is between the first threshold and the second threshold, the processor 130 will not switch from the monitoring state to the alerting state, and the activation of first trigger unit 120 will not generate any effect on adhesive thermometer patch 100.

In some embodiments, the predetermined time period is at least 10 minutes. In some embodiments, the predetermined time period is selected from the range of 15 to about 60 minutes. In further embodiments, the predetermined time period is selected from the range of 20 to 40 minutes. In some embodiments, the predetermined time period is about 30 minutes. In some embodiments, the predetermined time period is in the range of 10 minutes to 3.5 hours, 15 minutes to 3 hours, 15 minutes to 2.5 hours, 15 minutes to 2 hours, 20 minutes to 1.5 hours, 20 minutes to one hour, 20 minutes to 45 hours, 25 minutes to 35 minutes, or about 30 minutes. Each possibility represents a separate embodiment.

In some embodiments, power supply unit 112 comprises at least one battery. In further embodiments, power supply unit 112 comprises a lithium-based coin cell, such as but not limited to, a model CR2012, configured to provide long-term power to adhesive thermometer patch 100. In some embodiments, power supply unit 112 is configured to provide power to: temperature sensor 110, control unit 116, audible indication unit 118, and at least one visual indicator 122, for at least about 48 hours of continuous operation. In further embodiments, power supply unit 112 is configured to provide power to temperature sensor 110, control unit 116, audible indication unit 118, and at least one visual indicator 122, for at least about 72 hours of continuous operation.

In some embodiments, the power supply unit 112 is configured to enable at least about 72 hours of continuous operation for all of the electronic components of adhesive thermometer patch 100. In further embodiments, the power supply unit 112 is configured to enable up to about 72 hours of continuous operation for all of the electronic components of adhesive thermometer patch 100. In still further embodiments, power supply unit 112 comprise a battery, configured to enable up to about 72 hours of continuous operation for each one of temperature sensor 110, control unit 116, audible indication unit 118, and at least one visual indicator 122.

Advantageously, since during the suspension state almost all of adhesive temperature patch 100 components are deactivated (except for the power supply unit 112 and processor 130 comprising timer 134), the utilization of the suspension state can prolong/extend the availability of the power supply unit 112, and as a result to prolong/extend the continuous operation of the adhesive thermometer patch 100. In some embodiments, the utilization of the suspension state is configured to prolong the at least one battery's life and decrease power consumption of the adhesive thermometer patch 100.

As used herein, the terms "power" and "energy" are interchangeable, and refer to electrical energy such as electricity provided by power supply unit 112.

In some embodiments, the capacity of the battery is in the range of about 100 to about 600 mAh. In some embodiments, the capacity of the battery is in the range of about 200 to about 350 mAh. In still further embodiments, the capacity of the battery is in the range of about 250 to about 300 mAh. Advantageously, the high capacity of the battery can enable up to about 72 hours of continuous operation for all of the electronic components of adhesive thermometer patch 100.

In some embodiments, the LED lamp of visual indicator 122 does not display any color in between temperature measurements, when processor 130 identifies temperature signals indicating a temperature between the first threshold and the second threshold, in order to decrease power consumption of power supply unit 112.

In some embodiments, following the consumption or the discharge of power supply unit 112, the at least one visual indicator 122 is turned off. It is contemplated that the lack of visual indication of the operation of adhesive thermometer patch 100 can indicate that the adhesive thermometer patch 100 needs to be replaced.

It is contemplated that the at least one visual indicator 122 can provide a visual indication of the continuous operation of adhesive thermometer patch 100 as was described herein above, thereby informing or alerting external users of the temperature of the user wearing the patch (e.g., green light during measurement of normal body temperature, and red light for measurement of critical temperature). Advantageously, said visual indication can alert external users suffering from hearing problems or hearing loss regarding the condition of the user wearing the patch.

In some embodiments, adhesive thermometer patch 100 comprises a plurality of visual indicators 122. In some embodiments, adhesive thermometer patch 100 comprises a plurality of LED lamps. In some embodiments, the at least one visual indicator 122 comprises a first visual indicator comprising a first LED lamp, and a second visual indicator comprising a second LED lamp. In some embodiments, the first LED lamp is configured to display a flashing green light during temperature measurements in the monitoring state. In some embodiments, the second LED lamp is configured to flash a red light during the alerting state.

Usage of adhesive thermometer patch 100 is advantageously configured to meet two opposing design criteria: keeping the patch small and affordable, while at the same time providing sufficient battery power to last for up to about 72 hours of continuous operation. Patch lifetime comprises shelf life, defined as the time on the shelf prior to first activation, followed by actual continued usage period after the first activation of at least one of power supply unit 112 and control unit 116. In some embodiments, the shelf life is in the range of 1 to 5 years. In some embodiments, the shelf life is in the range of 2 years to 3 years.

In some embodiments, first trigger unit 120 is configured to activate the various components of adhesive thermometer patch 100 upon first activation by the user, i.e. to switch the processor 130 from the deactivated state to the active state, and is further configured to cause processor 130 to switch from the alerting state to the suspension state, upon additional activation by the user.

The term "activation by the user" as used herein, refers to a user or an external user placing at least one finger on a surface of first trigger unit 120, wherein first trigger unit 120 is a push button switch, and pressing the button in the direction perpendicular to adhesive surface 102 towards the user's body.

In some embodiments, following the first activation by the user, adhesive thermometer patch 100 is configured for continuous operation, until the exhaustion or discharge of power supply unit 112. In some embodiments, adhesive thermometer patch 100 is configured for disposable use.

In some embodiments, adhesive thermometer patch 100 further comprise a second trigger unit (not shown), comprising an on/off push button switch. The term "on/off push button switch" as used herein refers to a two-position, 'on/off' switch mechanism, wherein a first press of the push button actuates the switch from 'off' to 'on' and activates the various components of adhesive thermometer patch 100, while a second press of the push button turns the switch back 'off' and deactivates the various components thereof. In further embodiments, the second trigger unit is configured to activate the various components of adhesive thermometer patch 100 upon first activation by the user. In further such embodiments, first trigger unit 120 is configured to solely switch from the alerting state to the suspension state, upon activation by the user or external users.

In some embodiments, minimization of power drain during device lifetime is achieved by an initialization mechanism, said initialization mechanism is configured to provide power to the components of adhesive thermometer patch 100 only from the moment it is extracted from its packaging. In further embodiments, power supply unit 112 activation comprises the steps of placing an insulating tab between at least one of two contacts (not shown) leading to suspension of power supply unit 112. In accordance with these embodiments, the removal of said insulating tab leads to direct connectivity between these contacts and the power supply unit 112, thereby closing an electrical circuit. In still further embodiments, at least one of said contacts is a spring-loaded to displace towards the other contact upon removal of said tab. In some embodiments, the tab is attached to the packaging (not shown) of adhesive thermometer patch 100, such that the tab is automatically removed on the instant of removing adhesive thermometer patch 100 from its packaging, thereby resulting in activation of power supply unit 112. In some other embodiments, the tab is not attached to the packaging (not shown) of adhesive thermometer patch 100, such that the tab has to be manually removed from thermometer patch 100 by the user or external user, thereby resulting in the initial activation of power supply unit 112.

In some embodiments, adhesive thermometer patch 100 further comprises a plastic or paper shield, configured to be reversibly attached to the adhesive surface 102, in order to protect the adhesive surface 102 prior to removing adhesive thermometer patch 100 from its packaging and the first activation of power supply unit 112, thereby prolonging the shelf life of the adhesive thermometer patch 100. In some embodiments, the removal of the plastic or paper shield is configured to initiate the first activation of adhesive thermometer patch 100, i.e. to switch the processor 130 from the deactivated state to the active state.

In some embodiments, upon first activation, processor 130 is configured to initiate a first activation command to audible indication unit 118, wherein said first activation command results in a short audible tone (i.e., a beep), in order to alert the user/external user of the successful initial activation of adhesive thermometer patch 100.

Reference is now made to FIG. 3, showing a flowchart illustrating a method for measuring the body temperature of a user 200, utilizing adhesive thermometer patch 100 as disclosed herein, in some embodiments.

In some embodiments, method 200 comprises step 202 of placing adhesive thermometer patch 100 as presented herein above on the skin of a user and attaching it thereto. In some embodiments, method 200 further comprises step 204 of initializing an activation of adhesive thermometer patch 100 by the user or external user, optionally by pressing first trigger unit 120, thereby switching processor 130 from the deactivated state to the active state, as was described herein above.

In some embodiments, method 200 further comprises step 206 of the monitoring state, comprising performing temperature measurements every 5 seconds to 5 minutes, or preferably every about 30 seconds. In some embodiments, during step 206 of the monitoring state, the audible indication unit 118 is deactivated. In some embodiments, adhesive thermometer patch 100 comprises at least one visual indicator 122. In some embodiments, the at least one visual indicator 122 is a LED lamp. In some embodiments, the LED lamp displays a flashing green light during temperature measurements.

In step 208 it is determined whether the temperature of the skin of the user is above the first threshold or below the second threshold. If the temperature is between the first and the second thresholds (step 208—No), method 200 returns back to step 206 of the monitoring state, as presented herein. In some embodiments, if the temperature of the skin of the user is between the first and the second thresholds, the method 200 returns from step 208 to step 206, for a new temperature measurement.

If the temperature of the skin of the user is indeed above the first threshold or below the second threshold (step 208—Yes), step 210 of the alerting state is activated, comprising activating audible indication unit 118. In some embodiments, step 210 of alerting state further comprises switching the LED lamp to a flashing red light.

In some embodiments, following step 210, method 200 further comprises step 212 of activating first trigger unit 120 by the user or an external user, thereby switching adhesive thermometer patch 100 from the alerting state to a suspension state, for a predetermined time period. In some embodiments, during the suspension state the audible indication unit 118, temperature sensor 110, first trigger unit 120, and the LED lamp are deactivated. In some embodiments, the predetermined time period is selected from the range of 15 to about 60 minutes, or preferably from the range of 20 to 40 minutes. During the predetermined time period, a medication or a treatment can be administered to the user.

In some embodiments, method 200 further comprises step 214 of switching adhesive thermometer patch 100 from the suspension state back to the monitoring state, following the predetermined time period. In some embodiments, step 214 of switching adhesive thermometer patch 100 from the suspension state back to the monitoring state comprises activating temperature sensor 110, first trigger unit 120, and the LED lamp. In some embodiments, following step 214, method 200 returns back to step 206, of the monitoring state, as was presented herein, for a new temperature measurement. In some embodiments, after returning back to step 206, method 200 continues to step 208, followed by the repetition of method 200 as was presented herein.

In some embodiments, the present invention provides a method for measuring the skin temperature of a user, the method comprising the steps of: (a) providing adhesive thermometer patch 100 as was presented herein above and attaching it to the skin of the user, wherein the adhesive thermometer patch 100 comprises: control unit 116; temperature sensor 110; audible indication unit 118; and first trigger unit 120; (b) pressing first trigger unit 120 thereby initializing an activation of adhesive thermometer patch 100, wherein the activation comprises activating at least control unit 116 and temperature sensor 110; (c) performing temperature measurements of the skin of the user every 5 seconds to 5 minutes using temperature sensor 110, and transferring temperature signals corresponding thereto to control unit 116; (d) determining whether the temperature of the skin of the user is: above a first threshold, below a second threshold, or between the first and the second thresholds; (e) activating audible indication unit 118, if the temperature of the skin of the user is above the first threshold or below the second threshold; (f) pressing first trigger unit 120 if the audible indication unit is activated, thereby deactivating audible indication unit 118 for a predetermined time period; and (g) reactivating temperature sensor 110, following the ending of the predetermined time period at step (f).

The term "plurality", as used herein, means more than one.

The term "about", as used herein, when referring to a measurable value such as an amount, a temporal duration, and the like, is meant to encompass variations of ±10% as such variations are appropriate to the disclosed devices, systems and/or methods.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A self-contained adhesive thermometer patch comprising:
   an adhesive surface configured to be attached to a skin of a user and an opposing surface;
   a control unit;
   a non-invasive temperature sensor configured to measure temperatures in a range of 30° C. to 45° C., and to transfer temperature signals to said control unit, in response thereto; wherein the non-invasive temperature sensor is associated with or embedded into a portion of the adhesive surface so that at least a portion of the sensor is configured to contact the skin of the user non-invasively while the adhesive surface is attached to the skin of the user;
   a power supply unit;
   an audible indication unit; and
   a first trigger unit,
   wherein the adhesive surface and the opposing surface form a housing therebetween accommodating at least the control unit, the power supply unit, the audible indication unit, and the first trigger unit;
   wherein said control unit is configured to switch from a monitoring state to an alerting state upon receiving transferred temperature signals that indicate a temperature above a first threshold or below a second threshold,
   wherein the audible indication unit is deactivated in the monitoring state,
   wherein the control unit is configured to activate said audible indication unit in the alerting state, and
   wherein in the alerting state, upon activation of the first trigger unit, the control unit switches from the alerting state to a temporary suspension state for a predetermined time period in a range of 10 minutes to 4 hours, wherein in the temporary suspension state, the control unit is configured to deactivate at least the audible indication unit for the predetermined time period before automatically reactivating the audible indication unit.

2. The adhesive thermometer patch according to claim 1, wherein the control unit is provided in a deactivated state, wherein the first trigger unit is further configured to switch the control unit from the deactivated state to an active state, wherein the active state comprises the alerting state, the temporary suspension state, and the monitoring state.

3. The adhesive thermometer patch according to claim 2, wherein upon switching from the deactivated state to the active state, the control unit is configured to be in the monitoring state.

4. The adhesive thermometer patch according to claim 1, wherein the temperature sensor is configured to transfer the temperature signals to the control unit at repeating intervals of every 5 seconds to 5 minutes.

5. The adhesive thermometer patch according to claim 4, further comprising at least one visual indicator, wherein the control unit is configured to operate the at least one visual indicator to provide a first visual indication, upon receiving each one of the temperature signals, in the monitoring state.

6. The adhesive thermometer patch according to claim 5, wherein the control unit is further configured to operate the at least one visual indicator to provide a second visual indication, upon receiving the temperature signals indicating that the temperature is above the first threshold or below the second threshold, in the alerting state.

7. The adhesive thermometer patch according to claim 6, wherein in the temporary suspension state the control unit is further configured to deactivate the temperature sensor, the first trigger unit, and the at least one visual indicator.

8. The adhesive thermometer patch according to claim 1, wherein following said predetermined time period, the control unit is configured to switch from the temporary suspension state to the monitoring state.

9. The adhesive thermometer patch according to claim 1, wherein the temperature sensor is embedded into a portion of the adhesive surface.

10. The adhesive thermometer patch according to claim 1, wherein the housing comprises an opening located on the opposing surface, wherein the opposing surface comprises a circumferential external barrier surrounding the opening and extending upwards perpendicularly to the adhesive surface, wherein the first trigger unit is a push button switch, and wherein the circumferential external barrier surrounds the push button switch, thereby preventing accidental activation thereof.

11. The adhesive thermometer patch according to claim 1, wherein the control unit comprises a processor that is configured to switch from the monitoring state to the alerting state upon receiving at least two consecutive transferred temperature signals that indicate a temperature above the first threshold or below the second threshold.

12. The adhesive thermometer patch according to claim 1, wherein the first threshold is a temperature in a range of 38° C. to 39° C., and the second threshold is a temperature in a range of 35° C. to 36.5° C.

13. The adhesive thermometer patch according to claim 5, wherein the power supply unit comprises a battery, configured to enable up to about 72 hours of continuous operation for each one of the temperature sensor, the control unit, the audible indication unit, and the at least one visual indicator, wherein the battery has a capacity in a range of 200 to 350 mAh.

14. A method for measuring a user's skin temperature, the method comprising the steps of:
   (a) providing a self-contained adhesive thermometer patch and attaching it to the user's skin, wherein the adhesive thermometer patch comprises: a control unit; an adhesive surface; a non-invasive temperature sensor associated with or embedded into a portion of the adhesive surface so that at least a portion of the sensor is configured to contact the skin of the user non-invasively while the adhesive surface is attached to the user's skin; an audible indication unit; and a first trigger unit;
   (b) initializing an activation of the adhesive thermometer patch, upon pressing the first trigger unit, wherein the activation comprises activating the control unit and the temperature sensor;
   (c) performing temperature measurements of the user's skin every 5 seconds to 5 minutes using the temperature sensor, and transferring temperature signals corresponding thereto to the control unit;
   (d) determining whether the user's skin temperature is: above a first threshold, below a second threshold, or between the first and the second thresholds;
   (e) activating the audible indication unit, if the temperature of the user's skin is above the first threshold or below the second threshold;

(f) deactivating the audible indication unit for a predetermined time period upon pressing the first trigger unit when the audible indication unit is activated; and (g) reactivating the audible indication unit of the temperature sensor, automatically by the control unit, following the predetermined time period of deactivation of step (f).

15. The method according to claim 14, wherein the adhesive thermometer patch further comprises a power supply unit, at least one visual indicator, an adhesive surface, and an opposing surface, wherein the adhesive surface and the opposing surface form a housing therebetween accommodating at least one of the control unit and the power supply unit.

16. The method according to claim 15, wherein step (c) further comprises providing a first visual indication by the at least one visual indicator, and wherein during step (c) the audible indication unit is deactivated.

17. The method according to claim 14, wherein step (e) comprises activating the audible indication unit, if the temperature of the user's skin—is above the first threshold or below the second threshold and proceeding to step (f); or returning to step (c), if the temperature of the user's skin is between the first and the second thresholds.

18. The method according to claim 16, wherein step (e) further comprises providing a second visual indication by the at least one visual indicator.

19. The method according to claim 14, wherein the pressing of the first trigger unit in step (f) causes the control unit to deactivate the audible indication unit for the predetermined time period, and to deactivate at least one of the temperature sensor and the first trigger unit.

20. The method according to claim 14, wherein step (g) further comprises returning to step (c).

* * * * *